US011833128B2

(12) United States Patent
Yan et al.

(10) Patent No.: US 11,833,128 B2
(45) Date of Patent: Dec. 5, 2023

(54) KETONE CARBONYL-CONTAINING HYDROPHOBIC ANTITUMOR DRUG AND CONJUGATE THEREOF AS WELL AS NANO PREPARATION CONTAINING CONJUGATE, PREPARATION METHOD THEREFOR, AND APPLICATION THEREOF

(71) Applicant: Jiangsu Jibeier Pharmaceutical Co. Ltd., Zhenjiang (CN)

(72) Inventors: Deyue Yan, Shanghai (CN); Zhongyi Geng, Zhenjiang (CN); Yao Wang, Shanghai (CN); Xinyuan Zhu, Shanghai (CN); Wei Huang, Shanghai (CN); Yongfeng Zhou, Shanghai (CN)

(73) Assignee: Jiangsu Jibeier Pharmaceutical Co. Ltd., Zhenjiang (CN)

( * ) Notice: Subject to any disclaimer, the term of this patent is extended or adjusted under 35 U.S.C. 154(b) by 396 days.

(21) Appl. No.: 16/975,996

(22) PCT Filed: Mar. 5, 2019

(86) PCT No.: PCT/CN2019/077038
§ 371 (c)(1),
(2) Date: Aug. 26, 2020

(87) PCT Pub. No.: WO2019/170092
PCT Pub. Date: Sep. 12, 2019

(65) Prior Publication Data
US 2021/0000785 A1     Jan. 7, 2021

(30) Foreign Application Priority Data
Mar. 6, 2018 (CN) .......................... 201810185012.4

(51) Int. Cl.
| | |
|---|---|
| *A61K 31/337* | (2006.01) |
| *A61P 35/00* | (2006.01) |
| *A61K 47/26* | (2006.01) |
| *A61K 47/34* | (2017.01) |

(52) U.S. Cl.
CPC ............ *A61K 31/337* (2013.01); *A61K 47/26* (2013.01); *A61K 47/34* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,760,072 A | 6/1998 | de Bont et al. | |
| 8,138,361 B2 * | 3/2012 | Ballatore ............ | C07D 405/12 549/511 |
| 2004/0176270 A1 | 9/2004 | Chen et al. | |
| 2012/0071467 A1 | 3/2012 | Ikeda et al. | |
| 2018/0186823 A1 | 7/2018 | Kadiyala et al. | |
| 2020/0385403 A1 | 12/2020 | Kratz et al. | |

FOREIGN PATENT DOCUMENTS

| | | |
|---|---|---|
| CN | 1362956 A | 8/2002 |
| CN | 102188717 A | 9/2011 |
| CN | 104491875 A | 4/2015 |
| CN | 104857525 A | 8/2015 |
| CN | 105031666 A | 11/2015 |
| CN | 109395087 A | 3/2019 |
| EP | 2409977 A1 | 1/2012 |
| EP | 3009516 A1 | 4/2016 |
| EP | 3184540 A1 | 6/2017 |
| WO | WO 2016/209935 A1 | 12/2016 |
| WO | WO2016205738 A2 | 12/2016 |
| WO | WO 2019/108975 A1 | 6/2019 |

OTHER PUBLICATIONS

Mou et al., "A small molecule nanodrug consisting of amphiphilic targeting ligand-chemotherapy drug conjugate for targeted cancer therapy", Journal of Controlled Release 230 (2016) 34-44.
Vossen, L. et al., "Pegylated Dendritic Polyglycerol Conjugate Targeting Ncam-Expressing Neuroblastoma: Limitations and Challenges," Nano (2018) DOI: https://doi.org/10.1016/j.nano.2018.02.009.
Ferber, S., et al., "Co-targeting the tumor endothelium and P-selectin-expressing glioblastoma cells leads to a remarkable therapeutic outcome," eLife (2017). DOI: https://doi.org/10.7554/eLife.25281.
Mou, Q., et al., "A Small Molecule Nanodrug Consisting of Amphiphilic Targeting Ligand-Chemotherapy Drug Conjugate for Targeted Cancer Therapy," Journal of Controlled Release (2016). DOI: https://doi.org/10.1016/j.jconrel.2016.03.037.
Smith, III, et al., "Design, synthesis, and Evaluation of Carbamate-Substituted Analogues of (+)-Discodermolide."
International Search Report for corresponding PCT Appl No. PCT/CN2019/077038, dated May 21, 2019.
Abou Samra et al., "Dual inhibitors of the pro-survival proteins Bcl-2 and Mcl-1 derived from natural compound meiogynin A," *European J. of Med. Chem.* 148 (2018) 26-38.

(Continued)

*Primary Examiner* — Brian J Davis
(74) *Attorney, Agent, or Firm* — Fish & Richardson P.C.

(57) ABSTRACT

The present disclosure provides a ketone carbonyl-containing hydrophobic antitumor drug and a conjugate thereof as well as a nano preparation containing the conjugate, a preparation method therefor, and an application thereof. The conjugate is an amphipathic pH-responsive conjugate obtained by enabling a dehydration condensation reaction between a hydrazide-terminated polyethylene glycol and/or lactose hydrazide and the ketone carbonyl-introduced hydrophobic antitumor drug. The ketone carbonyl-introduced hydrophobic antitumor drug is obtained by reacting an isocyanate group in a compound containing isocyanate group and ketone carbonyl group with a hydroxyl on a hydroxyl-containing hydrophobic antitumor drug. The hydroxyl-containing hydrophobic antitumor drug includes at least one of paclitaxel, docetaxel, paclitaxel derivatives, or docetaxel derivatives. Compared with docetaxel, the ketone carbonyl-containing hydrophobic antitumor drug, the conjugate thereof and the nano preparation have higher antitumor activity.

4 Claims, 6 Drawing Sheets

(56) References Cited

OTHER PUBLICATIONS

Malki et al., "Synthesis and cytotoxic activity of MOM-ether analogs of isosteviol," *Bioorg. & Med. Chem. Lett.* 24 (2014) 1184-1187.
Smith, III, et al., "Design, synthesis, and Evaluation of Carbamate-Substituted Analogues of (+)-Discodermolide." *Org. Lett.* 2005, 7, 2, 311-314; Dec. 22, 2004. https://doi.org/10.1021/ol047686a.
Chinese Office Action, with translation thereof, for corresponding CN Appl No. 202111301775.9, dated Aug. 25, 2023.
Zhang et al., "Synthesis and Properties of Self-assembling Paclitaxel Prodrug," Department of Polymer Science and Engineering; Center for Bionanoengineering, Department of Chemical and Biochemical Engineering, Zhejiang University, Hangzhou 310027 China, translation of Abstract only, Journal of Functional Polymers (2013), 26(2), pp. 115-122.

* cited by examiner

KETONE CARBONYL-CONTAINING HYDROPHOBIC ANTITUMOR DRUG AND CONJUGATE THEREOF AS WELL AS NANO PREPARATION CONTAINING CONJUGATE, PREPARATION METHOD THEREFOR, AND APPLICATION THEREOF

CROSS-REFERENCE TO RELATED APPLICATIONS

The present application is the U.S. National Stage under 35 U.S.C. § 371 of PCT International Application No. PCT/CN2019/077038, filed on Mar. 5, 2019, which claims the benefit of Chinese Application No. 201810185012.4, filed on Mar. 6, 2018.The foregoing are incorporated herein by reference in their entirety.

TECHNICAL FIELD

The present disclosure belongs to the technical field of biomedicine, and specifically relates to a ketone carbonyl-containing hydrophobic antitumor drug, a conjugate obtained by a dehydration condensation reaction between a hydrazide-terminated polyethylene glycol and/or lactose hydrazide and the ketone carbonyl-introduced hydrophobic antitumor drug, a nano preparation containing the conjugate and a preparation method therefor, and application in the preparation of an antitumor drug.

BACKGROUND

Some hydrophobic antitumor drugs, such as paclitaxel and docetaxel, have good therapeutic effects on breast cancer, ovarian cancer, etc., however, due to their extremely poor water solubility, the paclitaxel injections (Taxol) and docetaxel injections (Taxoter) currently used clinically are those obtained by dissolving paclitaxel and docetaxel in a solution of polyoxyethylene castor oil (Cremophor EL) or Tween 80 mixed with anhydrous ethanol, and are diluted with normal saline or 5% glucose to an appropriate concentration before use. However, injections containing Cremophor EL or Tween 80 may bring about serious toxic and side effects on patients, and may bring about security risks to clinical application. Therefore, the development of safe and non-toxic dosage forms of paclitaxel and docetaxel has always been a hot spot in the research of tumor treatment.

In recent years, with the development of nano-technology, various carriers such as liposomes (Pharmaceutical Research, 1994, 11 (6), 889-896.), polymeric micelles (Journal of Controlled Release, 2005, 109 (1-3), 158-168.), nanoparticles (Small, 2009, 5, 1706-1721.) and the like have been developed to embed paclitaxel and docetaxel and facilitate their delivery in vivo. In addition to utilizing the physical embedding method for drug delivery in vivo, there are still a lot of research efforts made for attempting to connect a hydrophilic group to hydrophobic drugs paclitaxel and docetaxel by means of chemical bonding to form an amphipathic conjugated as a prodrug, which is then formed into micelles in an aqueous phase by various preparation methods of micelles. In this way, not only the water solubility of the drug is improved, but also the loss of a small-molecule drug during its delivery in vivo is reduced by the formation of nanoparticles.

According to the structural characteristics of paclitaxel and docetaxel, the design of the currently reported amphipathic conjugated prodrugs is usually introducing a water-soluble or targeting group at a hydroxyl position via ester bond. The resulting products release, through the hydrolysis of ester bond, prodrugs which then exert antitumor effects, but it is important that the hydrolysis rate of the ester bonds may greatly affect the antitumor activity of the prodrugs. Greenwald used low-molecular-weight polyethylene glycols (PEG, IL7, =350, 750, 2000, and 5000) to bind to the 7-OH of paclitaxel, so as to modify paclitaxel and thereby forming prodrugs. The products thereof had solubility that was 30000 times greater than that of paclitaxel, but lo almost lost the antitumor activity completely (Journal of Organic Chemistry, 1995, 60 (2), 331-336). If a high-molecular-weight PEG (40000) is used to react with the 2'-OH of paclitaxel, the resulting product is easily hydrolyzed to release paclitaxel, the in-vitro antitumor activity thereof is equivalent to that of the original paclitaxel, and the in-vivo anti-tumor effect thereof on leukemia tumor P388 is slightly higher than that of the original paclitaxel. However, on the one hand, a high-molecular-weight carrier would significantly reduce the drug-loading rate of a prodrug, and on the other hand, injection of a large amount of an inactive carrier material into the body may bring about toxic and side effects. Therefore, the development of novel prodrugs of paclitaxel, docetaxel and derivatives thereof with strong antitumor activity and good safety is an urgent need for clinical tumor treatment.

SUMMARY

Problems to be Solved by the Disclosure

The present disclosure provides a conjugate obtained by a dehydration condensation reaction between a hydrazide-terminated polyethylene glycol and/or lactose hydrazide and a ketone carbonyl-introduced hydrophobic antitumor drug, and a pH-responsive nano preparation containing the conjugate, so as to solve the technical problems existed in in-vivo delivery of the existing hydrophobic antitumor drugs, such as paclitaxel, docetaxel, and derivatives thereof, and improve the in-vivo antitumor activity of hydrophobic antitumor drugs, such as paclitaxel, docetaxel, and derivatives thereof. The present disclosure further provides a preparation method of a nano preparation containing the above conjugate, and its application in the preparation of an antitumor drug. In addition, the present disclosure further provides a ketone carbonyl-containing hydrophobic antitumor drug and a ketone carbonyl-containing docetaxel derivative.

Means for Solving the Problems

The first aspect of the present disclosure provides a conjugate, which is obtained by a dehydration condensation reaction between a hydrazide-terminated polyethylene glycol and/or lactose hydrazide and a ketone carbonyl-introduced hydrophobic antitumor drug. The dehydration condensation reaction occurs between a ketone carbonyl group and a hydrazide group. The conjugate is an amphipathic pH-responsive conjugate.

The ketone carbonyl-introduced hydrophobic antitumor drug is obtained by reacting an isocyanate group in a compound containing isocyanate group and ketone carbonyl group with a hydroxyl in a hydroxyl-containing hydrophobic antitumor drug.

The compounds containing isocyanate groups and ketone carbonyl groups include: p-isocyanate benzaldehyde, m-isocyanate benzaldehyde, o-isocyanate benzaldehyde, p-isocyanate acetophenone, m-isocyanate acetophenone, o-isocyanate acetophenone, p-isocyanate benzophenone, m-isocyanate benzophenone, and o-isocyanate benzophenone.

The hydroxyl-containing hydrophobic antitumor drug includes at least one of paclitaxel, docetaxel, a paclitaxel derivative, and a docetaxel derivative.

The hydrazide-terminated polyethylene glycol has a number average molecular weight of 148 to 100000, and 1<PDI<2.

The hydrazide-terminated polyethylene glycol has a chemical structure as represented by the following Formula I:

Formula I

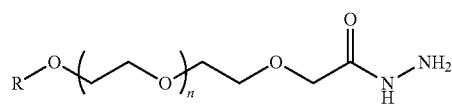

wherein R is H, —CH$_3$, or any group selected from the groups derived from biotin, folic acid, arginine-glycine-aspartic acid (RGD), floxuridine, cytarabine, gemcitabine, isatoribine, troxacitabine, hydroxyurea, mitoxantrone, ametantrone, streptozotocin, pingyangmycin, and bleomycin.

The lactose hydrazide has a chemical structure as represented by the following Formula II:

Formula II

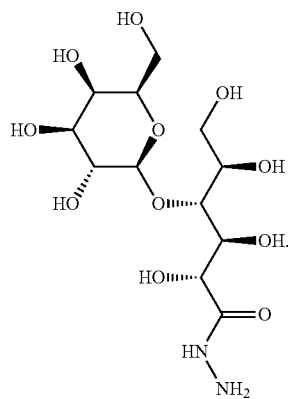

The paclitaxel derivative includes 10-deacetyl paclitaxel having a structure represented by Formula III, or cephalomannine having a structure represented by Formula IV:

Formula III

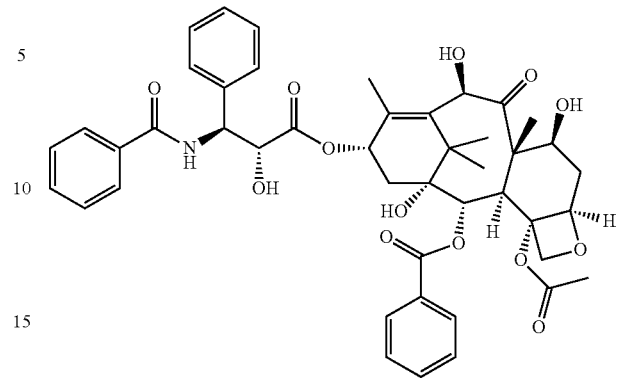

Formula IV

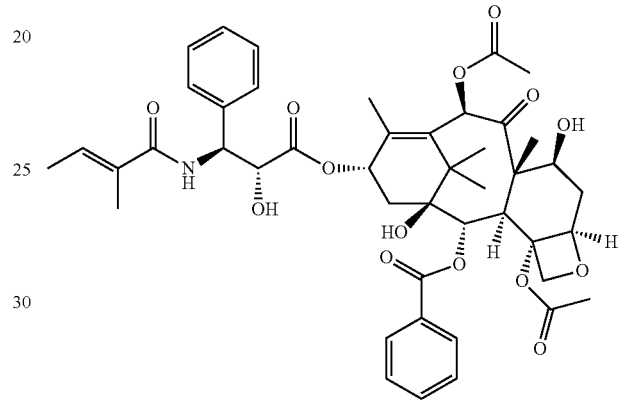

The docetaxel derivative has a structure represented by Formula V:

Formula V

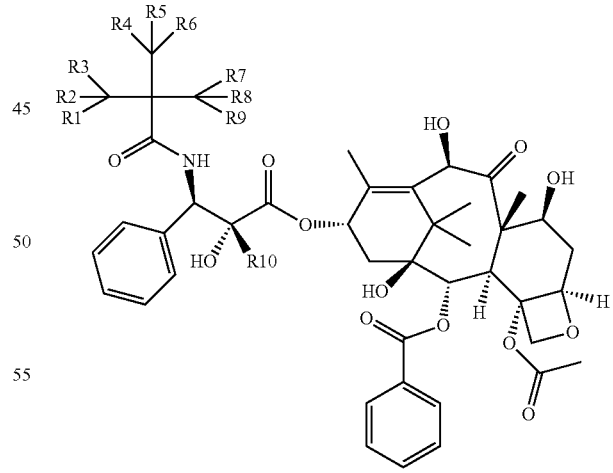

wherein R1, R2, R3, R4, R5, R6, R7, R8, R9 and R10 are each independently hydrogen, deuterium or fluorine, provided that at least one of them is deuterium or fluorine; preferably, wherein one or more of R1, R2, R3, R4, R5, R6, R7 R8 and R9 is deuterium, and R10 is deuterium.

The conjugates preferably include those having the structures represented by Formula (1) to Formula (7).

Formula (1)
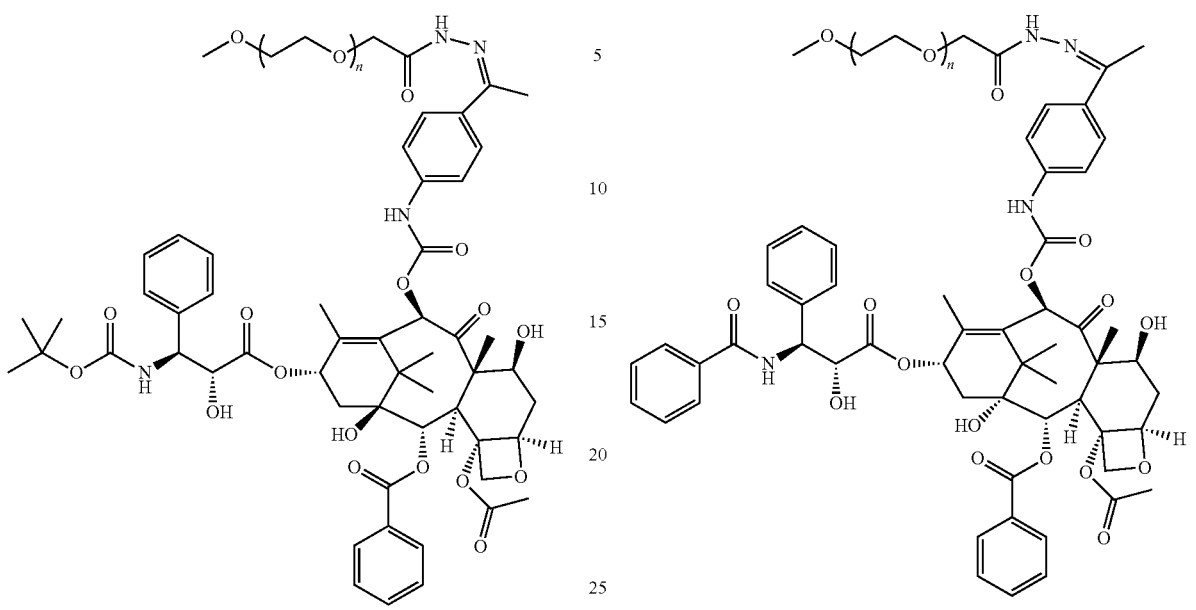
Formula (3)
Formula (2)
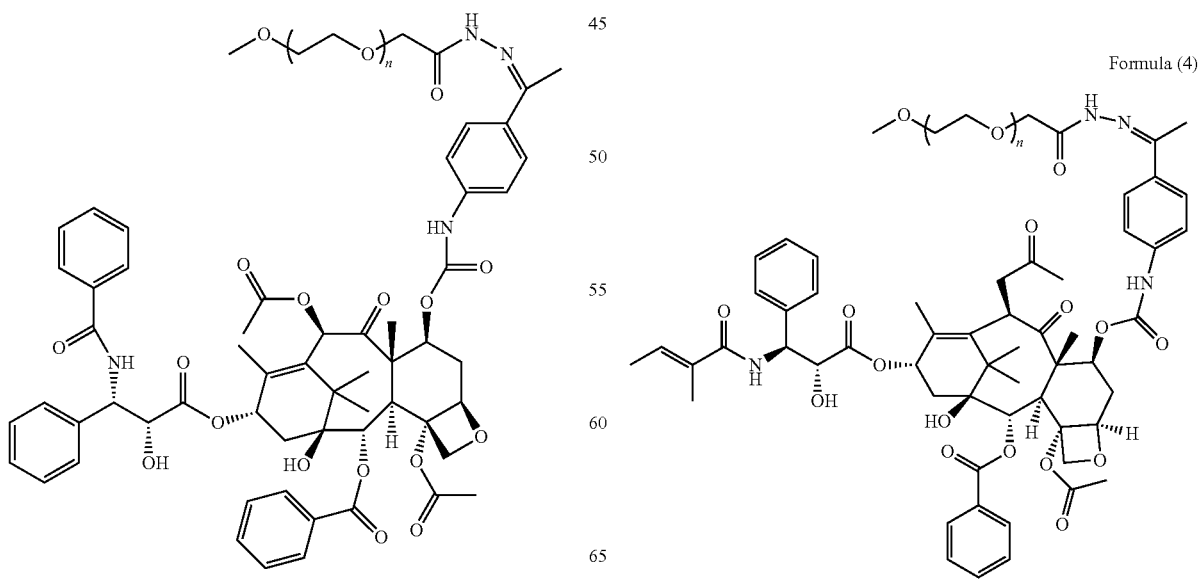
Formula (4)

Formula (5)

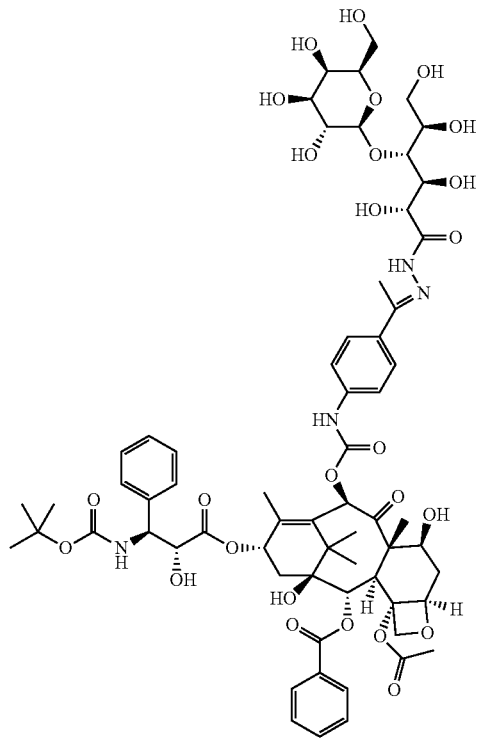

Formula (6)

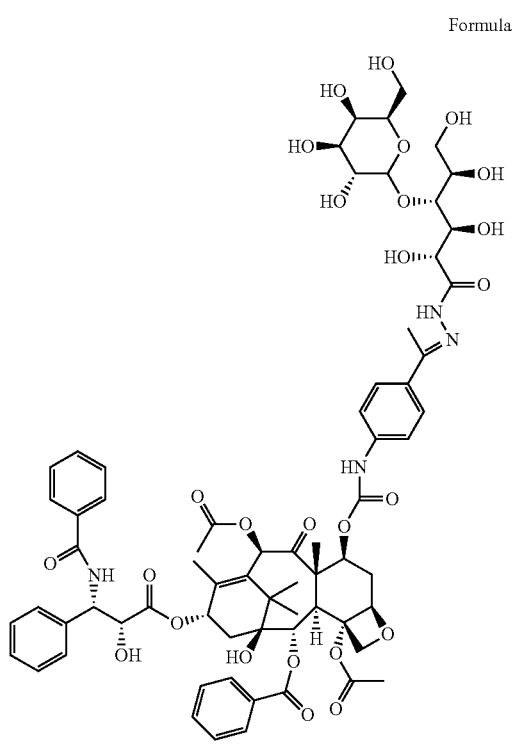

Formula (7)

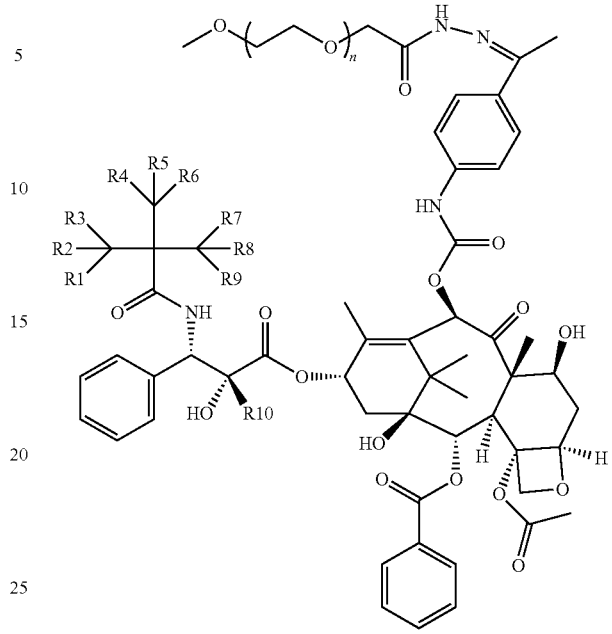

In Formula (7), R1, R2, R3, R4, R5, R6, R7, R8, R9 and R10 are each independently hydrogen, deuterium or fluorine, provided that at least one of them is deuterium or fluorine;

preferably, wherein one or more of R1, R2, R3, R4, R5, R6, R7, R8 and R9 is deuterium, and R10 is deuterium.

The second aspect of the present disclosure provides a nano preparation, comprising nanoparticles which comprise the above conjugate. The nanoparticles have a particle size of less to than 300 nm, preferably 20 to 200 nm. The nano preparation is a pH-responsive nano preparation.

The third aspect of the present disclosure provides a method for preparing the nano preparation, comprising the following steps:

step (1): subjecting the hydrazide-terminated polyethylene glycol and/or lactose hydrazide and the ketone carbonyl-introduced hydrophobic antitumor drug to the dehydration condensation is reaction, so as to obtain a conjugate; and step (2): dissolving the conjugate in an organic solvent to form a solution, adding the solution into water at room temperature, and removing the organic solvent to obtain an aqueous solution containing nanoparticles.

Preferably, in the step (1), an organic solution containing the hydrazide-terminated polyethylene glycol and/or lactose hydrazide is added into an organic solution of the ketone carbonyl-introduced hydrophobic antitumor drug, and the resulting mixture is stirred for reaction.

Preferably, the organic solvent in the step (1) and the step (2) is at least one selected from N,N'-dimethylformamide, dimethyl sulfoxide, tetrahydrofuran, acetonitrile, methanol, and dioxane.

The fourth aspect of the present disclosure provides use of the conjugate or the nano preparation in the preparation of an antitumor drug.

The fifth aspect of the present disclosure provides a ketone carbonyl-containing hydrophobic antitumor drug, which is obtained by reacting an isocyanate group in a compound containing isocyanate group and ketone carbonyl group with a hydroxyl in a hydroxyl-containing hydrophobic antitumor drug.

The hydroxyl-containing hydrophobic antitumor drug is at least one selected from paclitaxel, docetaxel, a paclitaxel derivative, and a docetaxel derivative.

The compounds containing isocyanate groups and ketone carbonyl groups include: p-isocyanate benzaldehyde, m-isocyanate benzaldehyde, o-isocyanate benzaldehyde, p-isocyanate acetophenone, m-isocyanate acetophenone, o-isocyanate acetophenone, p-isocyanate benzophenone, m-isocyanate benzophenone, and o-isocyanate benzophenone.

The paclitaxel derivative includes 10-deacetyl paclitaxel having a structure represented by Formula III, or cephalomannine having a structure represented by Formula IV:

Formula III

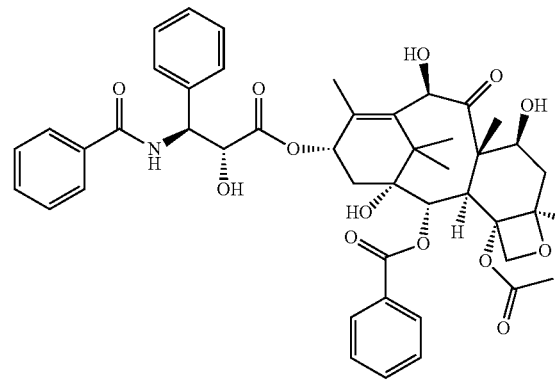

Formula IV

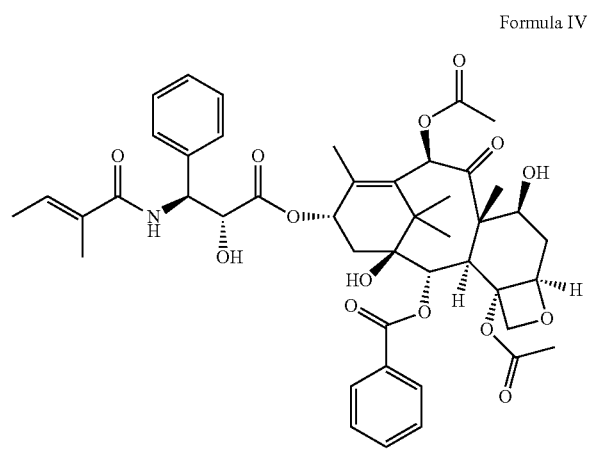

The docetaxel derivative comprises a structure represented by Formula V:

Formula V

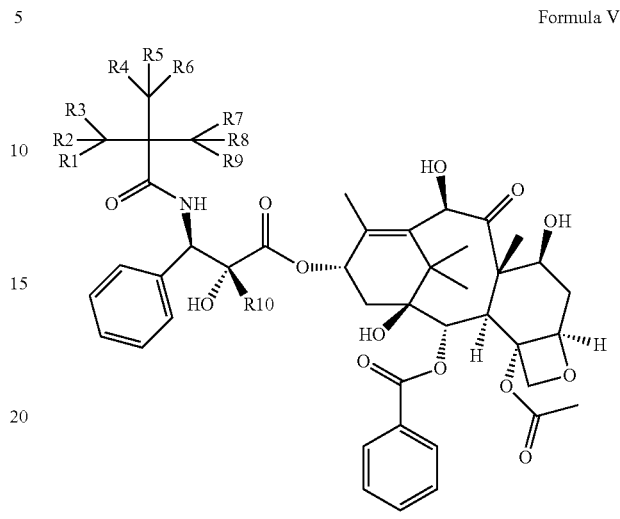

wherein R1, R2, R3, R4, R5, R6, R.7, R8, R9 and R10 are each independently hydrogen, deuterium or fluorine, provided that at least one of them is deuterium or fluorine; preferably, wherein one or more of R1, R2, R3, R4, R5, R6, R7, R8 and R9 is deuterium, and R10 is deuterium.

The sixth aspect of the present disclosure provides a ketone carbonyl-containing docetaxel derivative, which is obtained by reacting an isocyanate group in a compound containing isocyanate group and ketone carbonyl group with a hydroxyl in docetaxel or deuterated docetaxel; and the compounds containing isocyanate groups and ketone carbonyl groups include: p-isocyanate benzaldehyde, m-isocyanate benzaldehyde, o-isocyanate benzaldehyde, p-isocyanate acetophenone, m-isocyanate acetophenone, o-isocyanate acetophenone, p-isocyanate benzophenone, m-isocyanate benzophenone, and o-isocyanate benzophenone.

The deuterated docetaxel has a structure represented by Formula V.

Advantageous Effects of the Disclosure

Compared with the docetaxel preparations currently used in clinical practice, the ketone carbonyl-introduced hydrophobic antitumor drug and the pH-responsive nano preparation of the present disclosure have better anticancer activity and higher tumor inhibition rate during the treatment of malignant tumors, thus having potential clinical application value. The amphipathic pH-responsive conjugate of the present disclosure has a definite structure and may self-assemble in water to faun nanoparticles for delivery, thereby avoiding the toxic and side effects caused by the introduction of other carriers. The pH-responsive nanoparticles may passively target tumor tissues via the enhanced permeability and retention (EPR) effect of tumor tissues. Due to the slightly acidic environment in tumor tissues, the pH-responsive nanoparticles would be able to quickly release the hydrophobic antitumor drug molecules, thus avoiding the weakening or even loss of the antitumor activity caused by a lag of the release.

DETAILED DESCRIPTION

Figure 1:
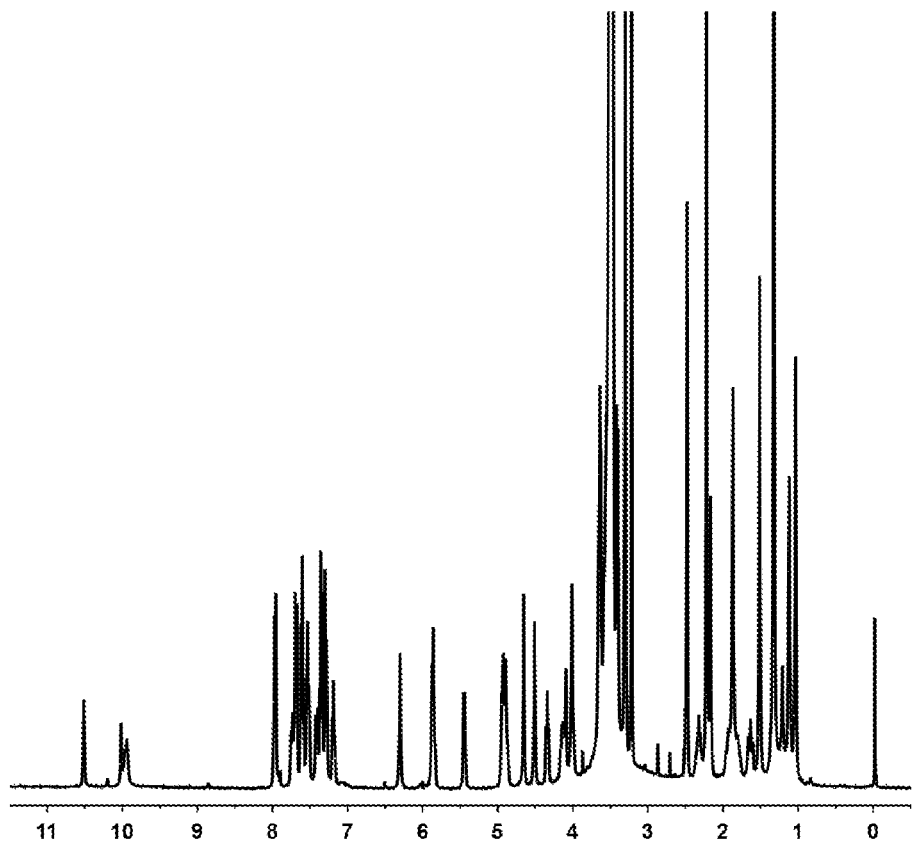
FIG. 1 is a $^1$H NMR spectrum of the amphipathic pH-responsive monomethylated PEG-docetaxel conjugate prepared in Example 1.

The conjugate of the present disclosure is obtained by a dehydration condensation reaction between a hydrazide-terminated polyethylene glycol and/or lactose hydrazide and a ketone carbonyl-introduced hydrophobic antitumor drug.

The ketone carbonyl-introduced hydrophobic antitumor drug is obtained by reacting an isocyanate group in a compound containing isocyanate group and ketone carbonyl group with a hydroxyl in a hydroxyl-containing hydrophobic antitumor drug. The hydroxyl-containing hydrophobic antitumor drugs may be hydroxyl-containing paclitaxel-based drugs and the derivatives thereof, and for example, may include at least one selected from paclitaxel, docetaxel, and the derivatives thereof.

Said derivatives include the optical isomers, pharmaceutically acceptable salts, solvates, hydrates, prodrugs, polymorphs, stereoisomers, geometric isomers or tautomers, deuterated products, and the like of the above compounds.

Said paclitaxel, docetaxel and the derivatives thereof not only have similar main structures, but also have basically the same mechanism of action. Therefore, conjugates and nano preparations may be formed by the method of the present disclosure to improve the efficacy of these drugs.

The hydrazide-terminated polyethylene glycol used in the present disclosure has a chemical structure as represented by the following Formula I:

Formula I

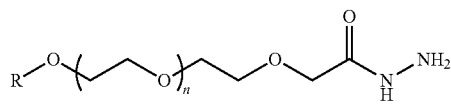

wherein R may be H or —CH$_3$, and may also be a group derived from a hydrophilic molecule or a hydrophilic drug, for example, any group of the groups derived from biotin, folic acid, arginine-glycine-aspartic acid (RGD), floxuridine, cytarabine, gemcitabine, isatoribine, troxacitabine, hydroxyurea, mitoxantrone, ametantrone, streptozotocin, pingyangmycin, bleomycin, etc.

The hydrazide-terminated polyethylene glycol used in the present disclosure has a number average molecular weight of 148 to 100000, and 1<PDI<2.

For a method for preparing the hydrazide-terminated polyethylene glycol, please refer to the Preparation Examples of the present application.

The lactose hydrazide used in the present disclosure has a chemical structure as represented by the following Formula II:

Formula II

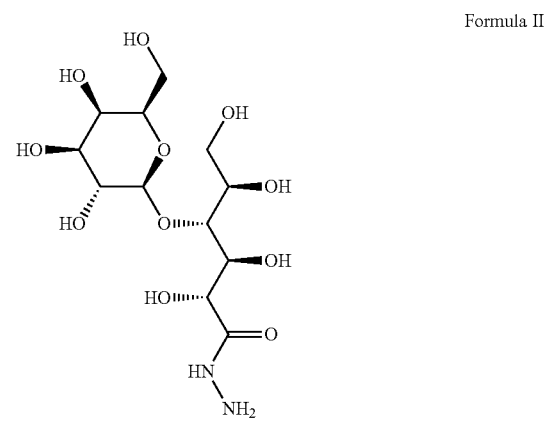 [SMILES: NNC(=O)[C@H](O)[C@H](O)[C@H](O[C@@H]1O[C@H](CO)[C@H](O)[C@H](O)[C@H]1O)[C@H](O)CO]

For a method for preparing lactose hydrazide, please refer to the Preparation Examples of the present application.

The paclitaxel derivatives as described in the present disclosure include 10-deacetyl paclitaxel and cephalomannine, which have chemical structures respectively represented by the following Formula III and Formula IV:

Formula III

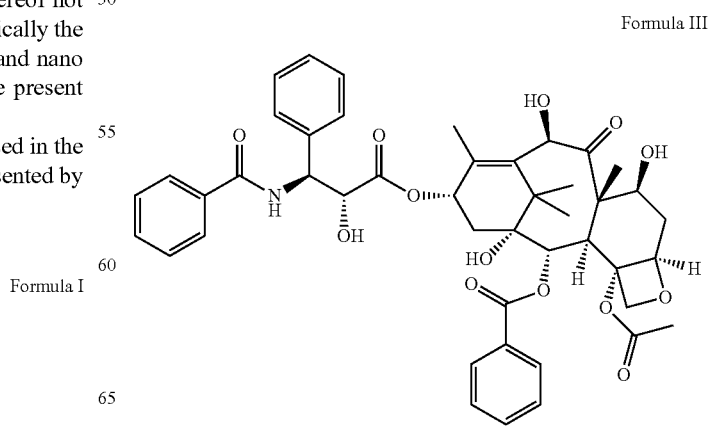

Formula IV

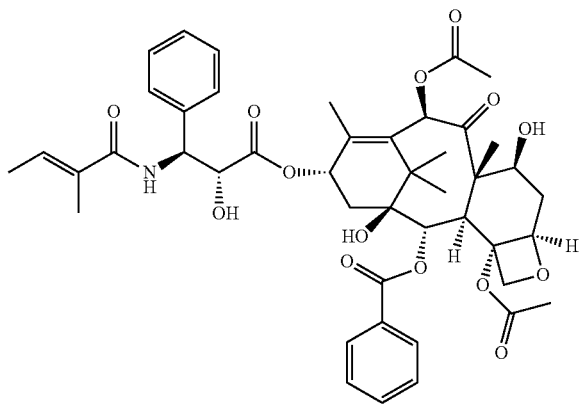

The docetaxel derivatives, including the deuterated derivatives of docetaxel, have chemical structures as represented by the following Formula V:

Formula V

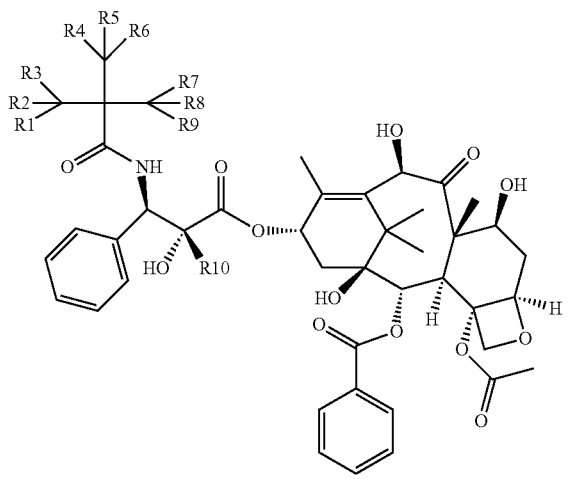

In Formula V, R1, R2, R3, R4, R5, R6, R7, R8 and R9 are each independently hydrogen, deuterium, or fluorine, and R10 is deuterium. Preferably, one or more of R1, R2, R3, R4, R5, R6, R7, R8 and R9 is deuterium; more preferably, R1, R2, R3, R4, R5, R6, R7, R8, R9 and R10 are all deuterium, or R1, R2, R3, R4, R5, R6, R7, R8 and R9 are all fluorine, and R10 is deuterium.

The above-mentioned derivatives of paclitaxel, 10-deacetyl paclitaxel, cephalomannine or docetaxel include the optical isomers, solvates, polymorphs, stereoisomers, geometric isomers or tautomers thereof.

The conjugate of the present disclosure is amphipathic since one end of the conjugate is a ketone carbonyl-introduced hydrophobic antitumor drug and the other end is a hydrophilic compound. The amphipathic structure allows the conjugate to (primarily) undergo hydrophobic association in water and self-assemble into nanomicelles.

The conjugate of the present disclosure is dissolved in an organic solvent to form a solution, the solution is added into water at room temperature, and the organic solvent is removed to obtain an aqueous solution containing nanoparticles. Among above steps, the conjugate is dissolved in an organic solvent at a concentration ranging from 2 ng/ml to 70 mg/ml, preferably at a concentration ranging from 3 μg/ml to 35 mg/ml, and the ratio (volume ratio) of the resulting solution to water may be 1:1 to 1:50, and preferably 1:2 to 1:10. The method for removing the organic solvent may be a method commonly used in the prior art, such as vacuum distillation etc. In a nano preparation containing the conjugate of the present disclosure, the content of the ketone carbonyl-introduced hydrophobic antitumor drug is 0.8 ng/ml to 20 mg/ml, and preferably 1 μg/ml to 10 mg/ml. The content of the ketone carbonyl-introduced hydrophobic antitumor drug in the nano preparation may be adjusted according to specific applications.

The therapeutic dose of the nano preparation of the present application may be determined according to the specific therapeutic use, the type and development of the disease, the patient's health status, and the judgment of the physician. Some typical dose ranges are 40 to 300 mg/kg body weight/day, and preferably 200 mg/kg body weight/day.

Preparation Examples and Examples are given below and the technical solutions of the present disclosure are further explained with reference to the drawings. However, the following Preparation Examples and Examples are merely exemplary illustration of the present disclosure, and should not be construed as limitations to the protection scope of the present disclosure. Some non-essential improvements and adjustments to the present disclosure made by those skilled in the art based on the above contents of the present disclosure still fall within the protection scope of the present disclosure.

Unless otherwise stated, the starting materials used are all commercially available starting materials.

Notes on some starting materials:

Polyethylene glycol monomethyl ether ($M_n$=2000): purchased from Sigma-Aldrich Corporation Carboxyl-terminated monohydroxy polyethylene glycol ($M_n$=2000), purchased from Sigma-Aldrich Corporation Lactobionic acid: purity: 97%, purchased from Adamas Pharmaceuticals, Inc.

Docetaxel: purity: 98%, purchased from Jiangsu Yew Pharmaceutical Co., Ltd.

Paclitaxel: purity: 98%, purchased from Jiangsu Yew Pharmaceutical Co., Ltd.

Preparation Examples of Synthesizing Hydrazide-Terminated Polyethylene Glycol

Preparation Example 1

Polyethylene glycol monomethyl ether (20 g, 10 mmol) was completely dissolved in toluene (200 mL), the air in the reaction flask was removed by introducing nitrogen, and a solution of potassium tert-butoxide (4.12 g, 36 mmol) in tert-butanol (60 mL) was gradually added dropwise. After half an hour of reaction, ethyl bromoacetate (6.4 mL, 48 mmol) was added dropwise over half an hour, and the reaction solution was reacted at room temperature for 24 hours. After the completion of the reaction, the reaction solution was filtered through a Buchner funnel. The filtrate was concentrated, and then precipitated three times in ice-cold diethyl ether. The white precipitate was subjected to vacuum drying at 35° C. for 24 hours, and finally ethyl acetate-terminated polyethylene glycol monomethyl ether was obtained with a yield of 90%.

¹H NMR (400 MHz, DMSO-d₆, 20° C.): δ=1.18 (t, J =7.04 Hz, 3H; CH₃), 3.22 (s, 3H; OCH₃), 3.31-3.66 (m, 180H; OCH₂CH₂), 4.22 (m, 2H; OCH₂CH₂OCO), 4.70 (s, 2H; OCOOCH2).

Subsequently, ethyl acetate-terminated polyethylene glycol monomethyl ether (10.00 g, 4.8 mmol) was dissolved in methanol (100 mL), and a solution of hydrazine hydrate (30 mL) in methanol (40 mL) was gradually added dropwise. After 24 hours of reaction, the reaction solution was filtered. The filtrate was concentrated, extracted three times with dichloromethane, dried over anhydrous magnesium sulfate, and subjected to suction filtration through a Buchner funnel. The filtrate was concentrated, and then precipitated in ice-cold diethyl ether. The white precipitate was subjected to vacuum drying at 35° C. for 24 hours, and finally hydrazide-terminated monomethylated polyethylene glycol was obtained with a yield of 90%.

¹H NMR (400 MHz, DMSO-d₆, 20° C.): δ=3.22 (s, 3H; OCH₃), 3.30-3.68 (in, 180H; OCH2CH2), 3.87 (s, 2H; OCH₂CH₂OCO), 8.87 (s, 1H; CONHNH₂).

Preparation Example 2 Carboxyl-terminated monohydroxy polyethylene glycol (10 g, 5 mmol) and 4-dimethylaminopyridine (DMAP) (61.1 mg, 0.5 mmol) were completely dissolved in methanol (100 mL), and a solution of dicyclohexylcarbodiimide (DCC) (2.1 g, 10 mmol) in methanol (20 ml) was slowly added dropwise thereto under ice bath conditions. After the dropwise addition was completed, the reaction solution was reacted at room temperature for 48 hours. After the completion of the reaction, the reaction solution was filtered through a Buchner funnel. The filtrate was concentrated, and then precipitated three times in ice-cold diethyl ether. The white precipitate was subjected to vacuum drying at 35° C. for 24 hours, and finally methyl ester-terminated monohydroxy polyethylene glycol was obtained with a yield of 76%.

Subsequently; methyl ester-terminated monohydroxy polyethylene glycol (5.00 g, 5 mmol) was dissolved in methanol (50 mL), and a solution of hydrazine hydrate (15 mL) in methanol (20 mL) was gradually added dropwise. After 24 hours of reaction, the reaction solution was filtered. The filtrate was concentrated, extracted three times with dichloromethane, dried over anhydrous magnesium sulfate, and subjected to suction filtration through a Buchner funnel. The filtrate was concentrated, and then precipitated in ice-cold diethyl ether. The white precipitate was subjected to vacuum drying at 35° C. for 24 hours, and finally hydrazide-terminated monohydroxy polyethylene glycol was obtained with a yield of 90%.

Preparation Example of Synthesizing Lactose Hydrazide

Preparation Example 3

Lactobionic acid (5.0000 g, 13.96 mmol) was dissolved in anhydrous methanol (70.0 mL) and the mixture was refluxed at 75° C. until lactobionic acid was completely converted to lactobionolactone.

¹H NMR (400 MHz, DMSO-d6) δ (ppm): 5.33-4.01 (br, OH), 4.34-4.13 (m, 2H, CH), 4.02-3.86 (m, 1H, CH), 3.75-3.25 (m, 10H, CH & CH2). ¹³C NMR (100 MHz, DMSO-d6) δ (ppm): 173.44, 105.42, 84.19, 76.01, 73.66, 71.83, 71.63, 71.41, 70.94, 68.55, 62.64, 60.79. The molecular weight of $C_{12}H_{19}O_{11}$ was 339.0927 as detected by HRMS: (ESI) [M−H]⁻.

At 25° C., lactobionolactone (3.0000 g, 8.82 mmol) was dissolved in anhydrous methanol (40.0 mL). Subsequently, hydrazine hydrate (2.2270 g, 44,10 mmol) was added dropwise to the reaction solution and the resulting mixture was reacted at 25° C. for 1 h. A white precipitate was generated. Vacuum distillation was carried out and lactose hydrazide was obtained as a white solid with a yield of 76.2%.

¹H NMR (400 MHz, DMSO-d6) δ (ppm): 8.91-8.50 (s, 1H, NH), 5.23-4.03 (br, OH), 4.32-4.17 (d, J=4.27 Hz, 1H, CH), 4.19-4.09 (d, J=4.16 Hz, 1H, CH), 4.04-3.93 (m, 1H, CH), 3.73-3.60 (m, 2H, CH), 3.60-3.46 (m, 5H, CH & CH2), 3.45-3.24 (m, 3H, CH), 3.18-3.16 (s, 2H, NH). ¹³C NMR (100 MHz, DMSO-d6) δ (ppm): 171.46, 104.95, 82.96, 76.15, 73.67, 72.05, 71.86, 71.56, 70.92, 68.74, 62.77, 61.15. The molecular weight of $C_{12}H_{20}O_{11}$ was 339.0927 as detected by HRMS: (ESI) [M±H]⁺.

Preparation Examples of Synthesizing Ketone Carbonyl-Introduced Hydrophobic Antitumor Drugs Preparation Example 4

6 g of docetaxel (DTX) was dissolved in 110 ml of a mixed solution of anhydrous dichloromethane and pyridine. Under ice bath conditions, 40 ml of triethylchlorosilane (TESCl) was added dropwise to the DTX solution at a dropwise addition rate of 10 ml/10 min for four times in total. After the dropwise addition was completed, stirring was continued for 40 min under ice bath conditions. Subsequently, the reaction system was placed in an oil bath at 35° C. and the mixture therein was further reacted for 24 h. After the completion of the reaction, water was added slowly so that no bubble was generated. Subsequently, the mixture was washed with water for 3 times, and dichloromethane was removed by vacuum distillation. The resulting mixture was subjected to gradient elution with ethyl acetate and petroleum ether, and triethylsilane-protected docetaxel (DTX-TES) as a white powdery solid was obtained via separation on a silica gel column with a yield of 98%.

¹H NMR (400 MHz, DMSO-d6) δ 8.01-7.94 (m, 2H), 7.72-7.66 (m, 1H), 7.59 (t, J=7.6 Hz, 2H), 7.48 (d, J=9.9 Hz, 1H), 7.38-7.30 (m, 4H), 7.16 (tt, J=6.0, 2.5 Hz, 1H), 5.86-5.74 (m, 1H), 5.39 (d, J=7.1 Hz, 1H), 4.92 (tt, J=12.6, 5.0 Hz, 4H), 4.50 (s, 1H), 4.45 (d, J=7.1 Hz, 1H), 4.29 (dd, J=10.5, 6.6 Hz, 1H), 4.03 (s, 2H), 3.65 (d, J =7.1 Hz, 1H), 2.34 (s, 4H), 1.91 (dd, J=15.3, 9.2 Hz, 1H), 1.71 1.57 (m, 4H), 1.53 (s, 3H), 1.34 (s, 9H), 0.96 (d, J=6.4 Hz, 6H), 0.87 (td, J=7.9, 2.2 Hz, 18H), 0.60-0.39 (m, 12H).

DTX-TES (2.06 g), 4-dimethylaminopyridine (25 mg), and p-isocyanate acetophenone (AI) (1.63 g) were dissolved in 100 ml of anhydrous N,N-dimethylformamide, and the mixture was slowly stirred until the solids were completely dissolved. After the dissolution was completed, the reaction system was placed in an oil bath at 56° C. and the mixture therein was reacted for 12 h. After the completion of the reaction, N,N-dimethylformamide was removed by vacuum distillation. The resulting mixture was subjected to gradient elution with ethyl acetate and petroleum ether, and was separated by column chromatography, thereby obtaining a white powdery solid (DTX-TES-AI) with a yield of 98%.

¹H NMR (400 MHz, DMSO-d6) δ 10.24 (s, 1H), 8.03-7.93 (m, 2H), 7.94-7.85 (m, 2H), 7.75-7.65 (m, 1H), 7.66-7.51 (m, 5H), 7.41-7.28 (m, 4H), 7.17 (tt, J=5.8, 3.0 Hz, 1H), 6.26 (s, 1H), 5.78 (t, J=9.1 Hz, 1H), 5.44 (d, J=7.1 Hz, 1H), 4.95 (d, J=9.1 Hz, 1H), 4.89 (dd, J=9.9, 7.1 Hz, 1H), 4.66 (s, 1H), 4.49-4.33 (m, 2H), 4.09-3.94 (m, 3H), 3.62 (d, J=7.0 Hz, 1H), 2.49 (s, 3H), 2.36 (d, J=5.4 Hz, 3H), 1.96 (s, 2H), 1.79 (s, 3H), 1.75-1.60 (m, 1H), 1.54 (s, 3H), 1.33 (s, 9H), 1.12 (d J=5.1 Hz, 3H), 0.98 (s, 3H), 0.85 (td, J=7.9, 6.2 Hz, 18H), 0.52 (kept, J=7.9 Hz, 12H).

DTX-TES-AI (2 g) was dissolved in 16 ml of 5% HCl/methanol, and the reaction was started at 26° C. After 30 min, 50 ml of ethyl acetate was added, the mixture was then washed with water for three times, and ethyl acetate was removed by vacuum distillation. The resulting mixture was subjected to gradient elution with ethyl acetate and petroleum ether, and was separated by column chromatography, thereby obtaining the target ketone carbonyl-introduced hydrophobic antitumor drug (DTX-AI), which was a white powdery solid, with a yield of 88%.

$^1$H NMR (400 MHz, DMSO-d6) δ 10.21 (s, 1H), 8.02-7.94 (m, 2H), 7.91 (d, J=8.7 Hz, 2H), 7.69 (t, J=7.4 Hz, 1H), 7.66-7.56 (m, 4H), 7.43 (d, J=9.4 Hz, 1H), 7.36 (t, J=7.6 Hz, 2H), 7.29 (d, J=7.6 Hz, 2H), 7.19 (t, J=7.2 Hz, 1H), 6.31 (s, 1H), 5.87 (td, J=9.6, 8.6, 5.5 Hz, 2H), 5.45 (d, J=7.1 Hz, 1H), 4.98 (d, J=6.9 Hz, 1H), 4.95-4.84 (m, 2H), 4.67 (s, 1H), 4.34 (t, J=7.2 Hz, 1H), 4.14 (dt, J=11.1, 7.0 Hz, 1H), 4.06-3.96 (m, 2H), 3.63 (d, J=7.0 Hz, 1H), 2.50 (s, 3H), 2.38-2.27 (m, 1H), 2.22 (s, 3H), 1.95-1.75 (m, 4H), 1.64 (t, J=12.5 Hz, 1H), 1.52 (s, 3H), 1.33 (s, 9H), 1.14 (d, J=10.9 Hz, 3H), 1.04 (s, 3H).

Preparation Example 5

6 g of paclitaxel (PTX) was dissolved in 110 ml of a mixed solution of anhydrous dichloromethane and pyridine. Under ice bath conditions, 40 ml of dimethyl tert-butyl chlorosilane (TBSCI) was added dropwise to the PTX solution at a dropwise addition rate of 10 ml/10 min for four times in total. After the dropwise addition was completed, stirring was continued for 40 min under ice bath conditions. Subsequently, the reaction system was placed in an oil bath at 35° C. and the mixture therein was further reacted for 24 h. After the completion of the reaction, water was added slowly so that no bubble was generated. Subsequently, the mixture was washed with water for 3 times, and dichloromethane was removed by vacuum distillation. The resulting mixture was subjected to gradient elution with ethyl acetate and petroleum ether, and was separated by column chromatography, thereby obtaining dimethyl tert-butyl silane-protected paclitaxel (PTX-TBS) as a white powdery solid with a yield of 98%.

$^1$H NMR (400 MHz, DMSO-d6) δ 8.81 (d, J=9.4 Hz, 1H), 8.01-7.92 (m, 2H), 7.87-7.79 (m, 2H), 7.70 (t, J=7.4 Hz, 1H), 7.58 (t, J=7.6 Hz, 2H), 7.55-7.42 (m, 5H), 7.38 (t, J=7.5 Hz, 2H), 7.19 (t, J=7.3 Hz, 1H), 6.24 (s, 1H), 5.83 (t, J=9.1 Hz, 1H), 5.52 (t, J=9.1 Hz, 1H), 5.40 (d,J=7.2 Hz, 1H), 4.94 (t, J=8.3 Hz, 2H), 4.76 (d, J=8.7 Hz, 1H), 4.68 (s, 1H), 4.05 (dq, J=27.1, 8.2, 7.1 Hz, 3H), 3.62 (d, J=7.1 Hz, 1H), 2.45 (s, 3H), 2.34 (d, J=9.4, 8.6 Hz, 1H), 2.07 (s, 3H), 1.94 (q, J=10.3, 7.2 Hz, 1H), 1.63 (t, J=12.2 Hz, 2H), 1.52 (s, J=17.6 Hz, 6H), 0.98 (d, J=15.6 Hz, 6H), 0.78 (s, 9H), 0.03 (d, J=16.1 Hz, 6H).

PTX-TBS (2.06 g), 4-dimethylaminopyridine (25 mg), and p-isocyanate acetophenone (AI) (1.63 g) were dissolved in 100 ml of anhydrous N,N-dimethylformamide, and the mixture was slowly stirred until the solids were completely dissolved. After the dissolution was completed, the reaction system was placed in an oil bath at 56° C. and the mixture therein was reacted for 12 h. After the completion of the reaction, N,N-dimethylformamide was removed by vacuum distillation. The resulting mixture was subjected to gradient elution with ethyl acetate and petroleum ether, and was separated by column chromatography, thereby obtaining a white powdery solid (PTX-TBS-AI) with a yield of 98%.

$^1$H NMR (400 MHz, DMSO-d6) δ 9.87 (s, 1H), 8.84 (d, J=9.4 Hz, 1H), 8.03-7.94 (m, 2H), 7.91-7.80 (m, 4H), 7.72 (t, J=7.3 Hz, 1H), 7.62 (t, J=7.6 Hz, 2H), 7.59-7.37 (m, 8H), 7.19 (t, J=7.4 Hz, 1H), 6.29 (s, 1H), 5.86 (t, J=9.1 Hz, 1H), 5.58-5.38 (in, 3H), 5.00 (d, J=9.4 Hz, 1H), 4.80-4.67 (m, 2H), 4.14-3.95 (m, 3H), 3.79 (d, J=7.0 Hz, 1H), 2.49 (s, 3H), 2.43 (s, 2H), 1.97 (s, 3H), 1.91 (dd, J=15.2, 9.6 Hz, 2H), 1.69 (d, J=15.6 Hz, 7H), 1.00 (d, J=6.5 Hz, 6H), 0.79 (s, 9H), 0.05 (d, J=23.3 Hz, 6H).

PTX-TBS-AI (2 g) was dissolved in 16 ml of 5% HCl/methanol, and the reaction was started at 26° C. After 30 min, 50 ml of ethyl acetate was added, the mixture was then washed with water for three times, and ethyl acetate was removed by vacuum distillation. The resulting mixture was subjected to gradient elution with ethyl acetate and petroleum ether, and was separated on a silica gel column, thereby obtaining the target ketone carbonyl-introduced hydrophobic antitumor drug (PTX-AI), which was a white powdery solid, with a yield of 88%.

$^1$H NMR (400 MHz, DMSO-d6) δ8.81 (d, J=9.4 Hz, 1H), 8.01-7.92 (in, 2H), 7.87-7.79 (m, 2H), 7.70 (t, J=7.4 Hz, 1H), 7.58 (t, J=7.6 Hz, 2H), 7.55-7.42 (m, 5H), 7.38 (t, J=7.5 Hz, 2H), 7.19 (t, I=7.3 Hz, 1H), 6.29 (s, 1H), 5.86 (t, J='9.1 Hz, 1H), 5.58-5.38 (m, 3H), 5.00 (d, J=9.4 Hz, 1H), 4.80-4.67 (m, 2H), 4.14-3.95 (in, 3H), 3.79 (d, J=7.0 Hz, 1H), 2.49 (s, 3H), 2.43 (s, 2H), 1.97 (s, 3H), 1.91 (dd, J=15.2, 9.6 Hz, 2H), 1.69 (d, J=15.6 Hz, 7H), 1.00 (d, J=6.5 Hz, 6H).

Examples of Synthesizing pH-Responsive Conjugates

EXAMPLE 1

The hydrazide-terminated monomethylated PEG (6 g) obtained in Preparation Example 1 was dissolved in 150 ml of anhydrous methanol. The ketone carbonyl-introduced docetaxel derivative (968.39 mg) obtained in Preparation Example 4 was dissolved in 20 ml of anhydrous methanol, and the resulting solution was added to the above solution containing the hydrazide-terminated monomethylated PEG. The mixture was stirred and reacted at room temperature under nitrogen protection for 48 hours. Methanol was removed by vacuum distillation. The mixture was subjected to gradient elution with acetonitrile and water, and was separated on a reversed-phase column, thereby obtaining a monomethylated PEG-docetaxel derivative conjugate (mPEG-DTX-AI) as a white powdery product with a yield of 90%.

The chemical structure of mPEG-DTX-AI synthesized in this example was as shown by Formula (1). The $^1$H NMR spectrum of the conjugate prepared in this example was as shown in FIG. 1, and the test solvent was DMSO-d6. The assignment of each proton peak in Spectrum 1 was shown as follows: $^1$H NMR (400 MHz, DMSO-d6) δ 10.51 (s, 1H), 10.06-9.87 (m, 2H), 7.97 (d, J=7.6 Hz, 2H), 7.74 (d, J=8.4 Hz, 1H), 7.69 (d, J=7.9 Hz, 2H), 7.60 (t, J=7.6 Hz, 2H), 7.52 (d, J=8.3 Hz, 2H), 7.41 (d, J=9.3 Hz, 1H), 7.35 (t, J=7.5 Hz, 2H), 7.29 (d, J=7.6 Hz, 2H), 7.19 (t, J=7.3 Hz, 1H), 6.30 (s, 1H), 5.87 (d, J=7.7 Hz, 2H), 5.44 (d, J=7.0 Hz, 1H), 4.99-4.83 (m, 3H), 4.65 (s, 1H), 4.51 (s, 1H), 4.34 (t, J=7.2 Hz, 1H), 4.11 (d, J=14.4 Hz, 2H), 4.01 (s, 2H), 3.64 (t, J=4.9 Hz, 2H), 3.49 (s, 195H), 3.22 (s, 3H), 2.32 (s, 1H), 2.22 (s, 3H), 2.17 (s, 3H), 1.87 (s, 4H), 1.63 (t, J=12.7 Hz, 1H), 1.51 (s, 3H), 1.33 (s, 9H), 1.12 (s, 3H), 1.03 (s, 3H).

Figure 2:
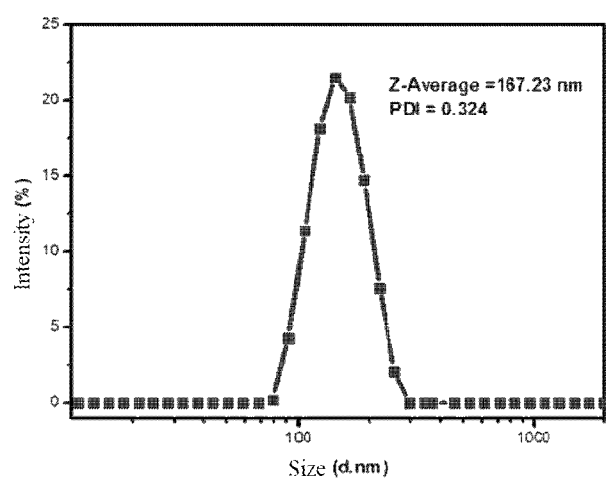
FIG. 2 is a graph showing the hydrodynamic diameter data of the nanoparticles prepared and obtained in Example 1.
Figure 3:
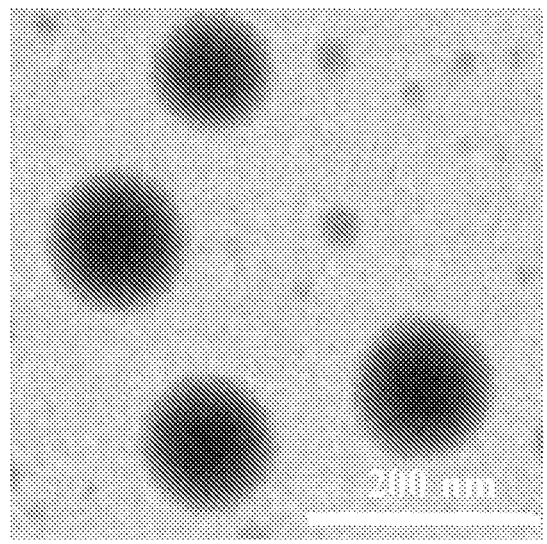
FIG. 3 is a transmission electron microscopic photograph of the nanoparticles prepared in Example 1.

The amphipathic conjugate prepared above was dissolved in tetrahydrofuran, and the mixture was added to water at room temperature. Tetrahydrofuran was removed and an aqueous solution of the nanoparticles of the amphipathic conjugate was obtained, in which the concentration of the docetaxel derivative was 1 mg/ml. The pH-responsive amphipathic conjugate-containing nanoparticles (Nano mPEG-DTX-AI) prepared in this example had an average particle size of about 170 nm. The hydrodynamic diameter data of the nanoparticles obtained in this example was as shown in FIG. 2, and the transmission electron microscopic photograph was as shown in FIG. 3.

EXAMPLE 2

The hydrazide-terminated monomethylated PEG (6 g) obtained in Preparation Example 1 was dissolved in 150 ml of anhydrous methanol. The ketone carbonyl-introduced paclitaxel derivative (1015.06 mg) obtained in Preparation Example 5 was dissolved in 20 ml of anhydrous methanol, and the resulting solution was added to the above solution containing the hydrazide-terminated monomethylated PEG. The mixture was stirred and reacted at room temperature under nitrogen protection for 48 hours. Methanol was removed by vacuum distillation. The mixture was subjected to gradient elution with acetonitrile and water, and was separated on a reversed-phase column, thereby obtaining a monomethylated PEG-paclitaxel derivative conjugate (mPEG-PTX-AI) as a white powdery product with a yield of 89%.

The chemical structure of the amphipathic pH-responsive monomethylated PEG-paclitaxel derivative conjugate synthesized in this example was as shown by Formula (2).

The amphipathic conjugate prepared above was dissolved in tetrahydrofuran, and the mixture was added to water at room temperature. Tetrahydrofuran was removed and an aqueous solution of the nanoparticles of the amphipathic conjugate was obtained, in which the concentration of the paclitaxel derivative was 1 mg/ml. The pH-responsive amphipathic conjugate-containing nanoparticles (Nano mPEG-PTX-AI) prepared in this example had an average particle size of about 200 nm.

EXAMPLE 3

The hydrazide-terminated monomethylated PEG (6 g) obtained in Preparation Example 1 was dissolved in 150 ml of anhydrous methanol to form a solution. A ketone carbonyl-introduced deuterated docetaxel derivative (968.39 mg) obtained in a manner similar to that in Preparation Example 4 was dissolved in 20 ml of anhydrous methanol, and the resulting solution was added to the above solution containing the hydrazide-terminated monomethylated PEG. The mixture was stirred and reacted at room temperature under nitrogen protection for 48 hours. Methanol was removed by vacuum distillation. The mixture was subjected to gradient elution with acetonitrile and water, and was separated on a reversed-phase column, thereby obtaining a monomethylated PEG-deuterated docetaxel derivative conjugate as a white powdery product with a yield of 90%.

The chemical structure of the amphipathic pH-responsive monomethylated PEG-deuterated docetaxel derivative conjugate synthesized in this example was as shown by Formula (7):

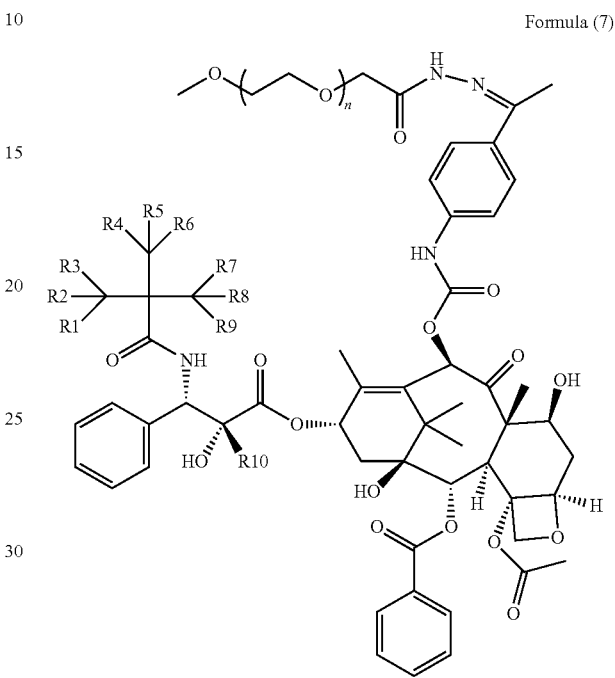

Formula (7)

wherein R1, R2, R3, R4, R5, R6, R7, R8, R9 and R10 were all deuterium.

The amphipathic conjugate prepared above was dissolved in tetrahydrofuran, and the mixture was added to water at room temperature. Tetrahydrofuran was removed and an aqueous solution of the nanoparticles of the amphipathic conjugate was obtained, in which the concentration of the deuterated docetaxel derivative was 1 mg/ml. The pH-responsive amphipathic conjugate-containing nanoparticles prepared in this example had an average particle size of about 200 nm.

EXAMPLE 4

The hydrazide-terminated monomethylated PEG (6 g) obtained in Preparation Example 1 was dissolved in 150 ml of anhydrous methanol to form a solution. A ketone carbonyl-introduced 10-deacetyl paclitaxel derivative (973.03 mg) obtained in a manner similar to that in Preparation Example 4 was dissolved in 20 ml of anhydrous methanol, and the resulting solution was added to the above solution containing the hydrazide-terminated monomethylated PEG. The mixture was stirred and reacted at room temperature under nitrogen protection for 48 hours. Methanol was removed by vacuum distillation. The mixture was subjected to gradient elution with acetonitrile and water, and was separated on a reversed-phase column, thereby obtaining a monomethylated PEG-10-deacetyl paclitaxel derivative conjugate as a white powdery product with a yield of 85%.

The chemical structure of the amphipathic pH-responsive monomethylated PEG-10-deacetyl paclitaxel derivative conjugate synthesized in this example was as shown by Formula (3):

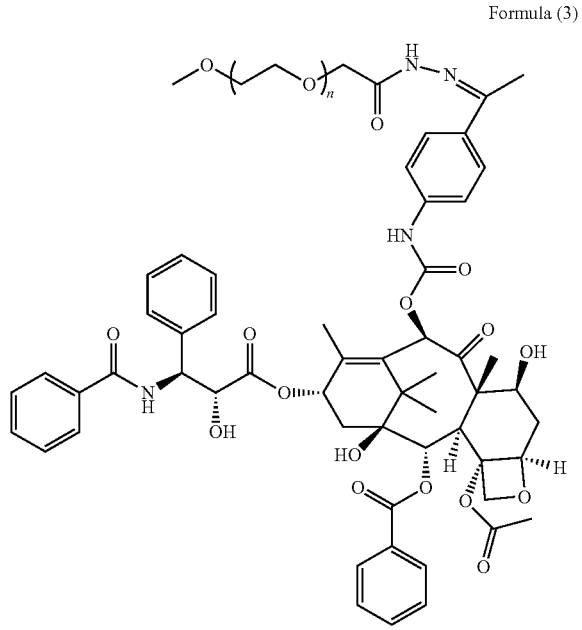

Formula (3)

The amphipathic conjugate prepared above was dissolved in tetrahydrofuran, and the mixture was added to water at room temperature. Tetrahydrofuran was removed and an aqueous solution of the nanoparticles of the amphipathic conjugate was obtained, in which the concentration of the 10-deacetyl paclitaxel derivative was 1 mg/ml. The pH-responsive amphipathic conjugate-containing nanoparticles prepared in this example had an average particle size of about 200 nm.

EXAMPLE 5

The hydrazide-terminated monomethylated PEG (6 g) obtained in Preparation Example 1 was dissolved in 150 ml of anhydrous methanol to form a solution. The ketone carbonyl-introduced cephalomannine derivative (992.39 mg) obtained in a manner similar to that in Preparation Example 4 was dissolved in 20 ml of anhydrous methanol, and the resulting solution was added to the above solution containing the hydrazide-terminated monomethylated PEG. The mixture was stirred and reacted at room temperature under nitrogen protection for 48 hours. Methanol was removed by vacuum distillation. The mixture was subjected to gradient elution with acetonitrile and water, and was separated on a reversed-phase column, thereby obtaining a monomethylated PEG-cephalomannine derivative conjugate as a white powdery product with a yield of 90%.

The chemical structure of the amphipathic pH-responsive monomethylated PEG-cephalomannine derivative conjugate synthesized in this example was as shown by Formula (4):

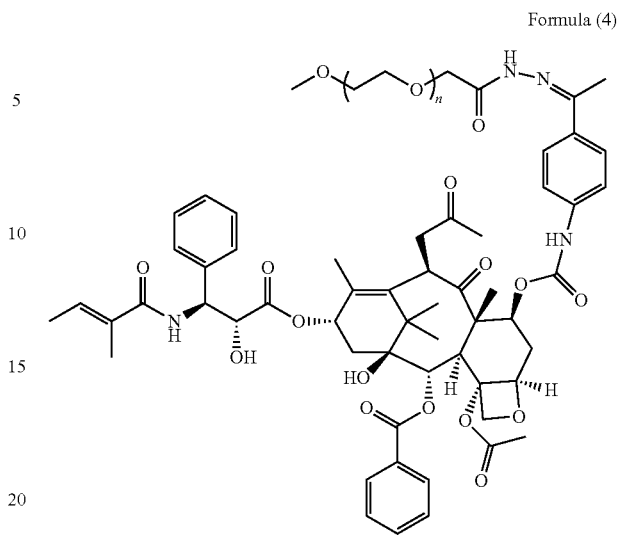

Formula (4)

The amphipathic conjugate prepared above was dissolved in tetrahydrofuran, and the mixture was added to water at room temperature. Tetrahydrofuran was removed and an aqueous solution of the nanoparticles of the amphipathic conjugate was obtained, in which the concentration of the cephalomannine derivative was 1 mg/ml. The pH-responsive amphipathic conjugate-containing nanoparticles prepared in this example had an average particle size of about 200 nm.

EXAMPLE 6

Lactose hydrazide (6 g) obtained in Preparation Example 3 was dissolved in 150 ml of anhydrous methanol. The ketone carbonyl-introduced docetaxel derivative (1015.06 mg) obtained in Preparation Example 4 was dissolved in 20 ml of anhydrous methanol, and the resulting solution was added to the above solution containing lactose hydrazide. The mixture was stirred and reacted at room temperature under nitrogen protection for 48 hours. Methanol was removed by vacuum distillation. The mixture was subjected to gradient elution with acetonitrile and water, and was separated on a reversed-phase column, thereby obtaining a lactose-docetaxel derivative conjugate as a white powdery product with a yield of 87%.

The chemical structure of the amphipathic pH-responsive lactose-docetaxel derivative conjugate synthesized in this example was as shown by Formula (5). The amphipathic conjugate prepared above was dissolved in tetrahydrofuran, and the mixture was added to water at room temperature. Tetrahydrofuran was removed and an aqueous solution of the nanoparticles of the amphipathic conjugate was obtained, in which the concentration of the docetaxel derivative was 1 mg/ml. The pH-responsive amphipathic conjugate-containing nanoparticles prepared in this example had an average particle size of about 200 nm.

EXAMPLE 7

Lactose hydrazide (6 g) obtained in Preparation Example 3 was dissolved in 150 ml of anhydrous methanol. The ketone carbonyl-introduced paclitaxel derivative (1015.06 mg) obtained in Preparation Example 5 was dissolved in 20 ml of anhydrous methanol, and the resulting solution was added to the above solution containing lactose hydrazide. The mixture was stirred and reacted at room temperature under nitrogen protection for 48 hours. Methanol was removed by vacuum distillation. The mixture was subjected to gradient elution with acetonitrile and water, and was separated on a reversed-phase column, thereby obtaining a lactose-paclitaxel derivative conjugate as a white powdery product with a yield of 85%.

The chemical structure of the amphipathic pH-responsive lactose-paclitaxel derivative conjugate synthesized in this example was as shown by Formula (6).

The amphipathic conjugate prepared above was dissolved in tetrahydrofuran, and the mixture was added to water at room temperature. Tetrahydrofuran was removed and an aqueous solution of the nanoparticles of the amphipathic conjugate was obtained, in which the concentration of the paclitaxel derivative was 1 mg/ml. The pH-responsive amphipathic conjugate-containing nanoparticles prepared in this example had an average particle size of about 200 nm.

Testing Method for the Hydrodynamic Diameter of the Nanoparticles of the Present Disclosure The average particle size (Z-Average) and the particle size distribution (PDI) of the nanomicelles were measured by dynamic light scattering (DLS), wherein the test temperature was 25° C., the wavelength of the laser was 633 nm, and the angle of the probe was 173°. Each sample was equilibrated for 2 min and tested for 3 times. The experimental data was analyzed by the software Dispersion Technology software version 5.32.

Testing Method of the Transmission Electron Microscopic Photograph of the Nanoparticles of the Present Disclosure The transmission electron microscopy (TEM) test was completed on a JEM-2010/INCA OXFORD model, wherein the accelerating voltage of the electron microscope was 200 kV. The method for preparing samples was as follows. The solution of assemblies was added dropwise onto a copper mesh coated with a carbon film, and the mesh was naturally air-dried at room temperature. Care should be taken to avoid contamination of impurities such as dust in the air during the drying process.

Pharmacodynamic Experiments

Experiment 1: Experiment on the Effects of the pH-Responsive Nano Preparations on Tumor In Vivo Hela tumor-bearing mice were divided into four groups with five mice in each group. The first, second, and third groups were the treatment groups, in which tumor treatment was carried out by respectively injecting the drug via the tail vein of each Hela tumor-bearing mouse. The first group was treated with the docetaxel injection (25 mg DTX/kg), the second group was treated with the antitumor drug DTX-AI obtained in Preparation Example 4 (40 mg DTX/kg), and the third group was treated by administering the pH-responsive nano preparation obtained in Example 1 (200 mg DTX/kg). The fourth group was the blank control group.

The mice in the first, second and third groups were treated by administering drugs once every seven days for a total of three injections. Each tumor-bearing mouse in each group was labeled, and the body weight and the tumor volume thereof throughout the treatment process were recorded. The tumor volume was calculated according to the following formula: V (mm$^3$)=½×length (mm)×width (mm)$^2$. The calculation formula of the relative tumor volume (RTV) was RTV=$V_t/V_0$, wherein $V_0$ was the tumor volume measured at the first administration after grouping (namely, $d_0$), and $V_t$ was the tumor volume at each measurement. On Day 45, the animals were sacrificed and dissected, the tumors were incised and weighed, and the body weights of the animals after tumor removal were calculated.

Figure 4:
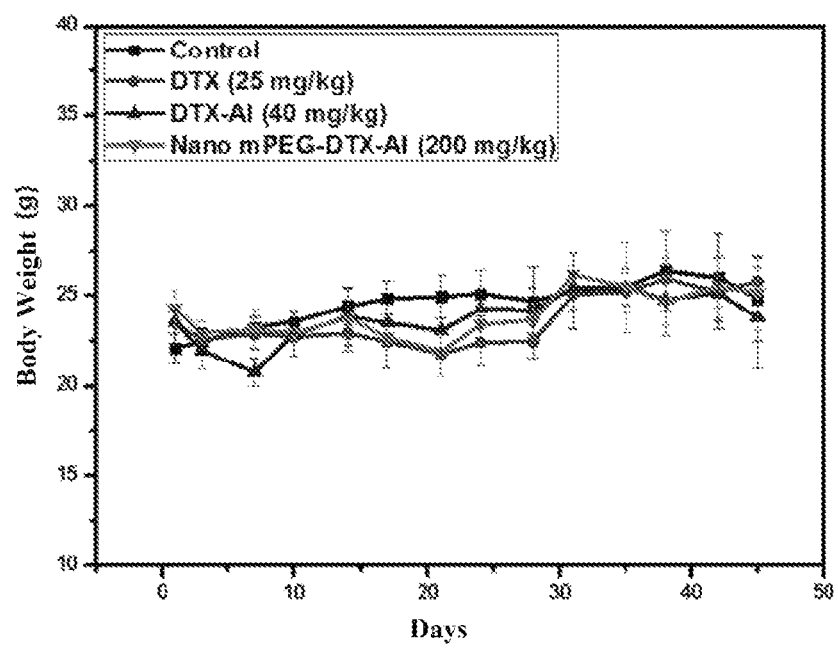
FIG. 4 shows the changes in body weights of the mice over treatment time.

FIG. 4 showed the changes in body weights of the mice over time. As shown in FIG. 4, the body weights of the mice in the second and third groups were basically the same as those in the blank control group, indicating that the in-vivo safety of DTX-AI and that of nano mPEG-DTX-AI were relatively high.

Figure 5:
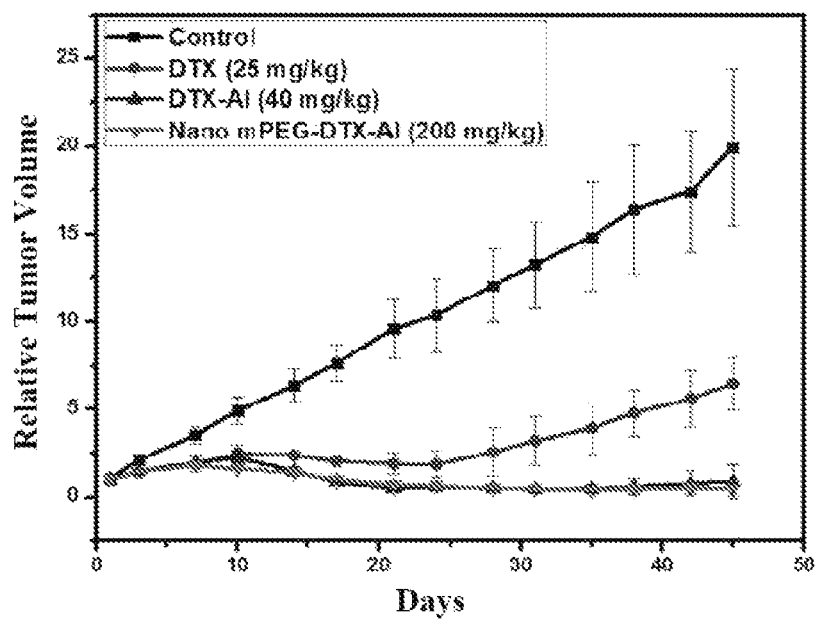
FIG. 5 shows the changes in relative tumor volume over treatment time.

FIG. 5 showed the changes in relative tumor volume over time. As shown in FIG. 5, as compared with the blank control group and the first group, the second and third groups showed a tendency of large decrease in relative tumor volume. In addition, after 21 days (after the administration was stopped), the relative tumor volumes of the first group continued to increase with time, the tumor inhibitory effect was gradually weakened, and a rebound phenomenon occurred. In contrast, the relative tumor volumes of the second and third groups still showed a decreasing trend with time, that is, after drug withdrawal, the tumor inhibitory effect continued to increase.

Figure 6:
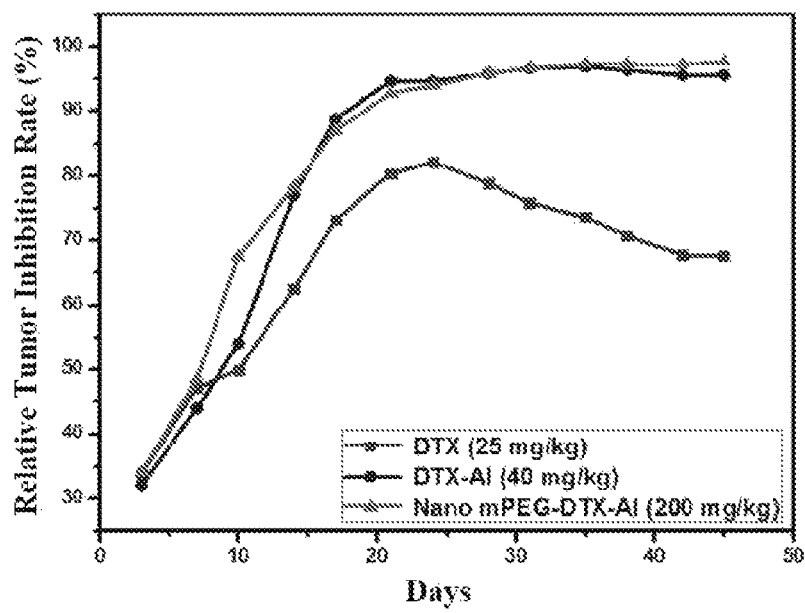
FIG. 6 shows the changes in relative tumor inhibition rate over treatment time.

Moreover, the relative tumor inhibition rate was also calculated and analyzed. The calculation formula of the relative tumor inhibition rate % was: relative tumor inhibition rate %=$(1-T_{RTV}/C_{RTV})*100\%$, (wherein TRW represented the RTV of a treatment group, and $C_{RTV}$ represented the RTV of the blank control group), and the results were as shown in FIG. 6.

The treatment groups all showed a tendency that the relative tumor inhibition rate increased continuously. Compared with the first group, the relative tumor inhibition rates of the second group and the third group showed substantial increases and continued to maintain at 90% or above after 21 days (after the administration was stopped). On the 30th day from the last administration, the relative tumor inhibition rate of the first group was 67.62%, the relative tumor inhibition rate of the second group reached 93.5%, and the relative tumor inhibition rate of the third group reached 95.61%.

Figure 7:
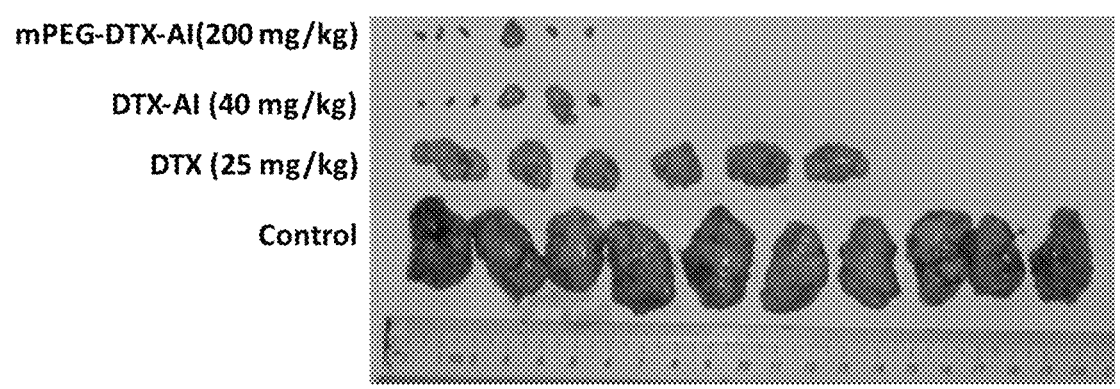
FIG. 7 is a photograph of the tumors in each group after the completion of the treatment.

FIG. 7 showed a photograph of the tumors in each group after the completion of the treatment. It was visually apparent from the photograph that the tumor sizes of the tumors in the second group and the third group were significantly smaller than those of the first group and the blank control group.

Experiment 2: Tumor Inhibitory Effect of Ketone Carbonyl-Introduced Hydrophobic Antitumor Drug (DTX-AI)

A well-grown A549 lung cancer solid tumor was taken and cut into uniform small masses having a size of about 3 mm under sterile conditions. Each mouse was inoculated subcutaneously under the right armpit with one mass by using a trocar. 14 days after inoculation, the average tumor volume was about 210 to 250 mm$^3$. The mice were grouped according to the tumor sizes, and the average tumor volume of each group was basically the same. The antitumor drug DTX-AI obtained in Preparation Example 4 was prepared into lyophilized powder for injection and administered, and the administration dosages were shown in Table 1 below. The long diameters (a) and the short diameters (b) of the tumors were measured with an electronic digital caliper twice a week. The calculation formula of tumor volume (TV) was: TV=½×a×b². The calculation formula of the relative tumor volume (RTV) was: RTV=$V_t/V_0$, wherein $V_0$ was the tumor volume measured at the time of grouping (namely, $d_0$), and $V_t$ was the tumor volume at each measurement. The evaluation index of antitumor activity was the relative tumor proliferation rate T/C (%) (T/C (%)=$T_{RTV}$/$C_{RTV}$×100%) or the relative inhibition rate of tumor proliferation (%), i.e., (1−T/C)×100%, and t test was conducted. On Day 43 (56 days after inoculation), the animals were sacrificed and dissected, the tumors were incised and weighed, and the body weights of the animals after tumor removal were calculated.

TABLE 1

| Group | Dose (mg/kg) | Dosage Regimen | Number of animals Start | Number of animals Final | Animal body weight (g) (After tumor removal) | RTV (Day 43) | Tumor inhibition rate % |
|---|---|---|---|---|---|---|---|
| Control (NS) | 10 ml/kg | iv × 4 (qw) | 12 | 12 | 25.76 ± 1.53 | 17.60 ± 5.15 | |
| Solvent control | 10 ml/kg | iv × 4 (qw) | 6 | 6 | 27.08 ± 1.51 | 18.71 ± 1.95 | 0 |
| Docetaxel L | 20 | iv × 4 (qw) | 6 | 6 | 25.35 ± 1.15 | 2.73 ± 1.36** | 84.50 |
| Docetaxel H | 40 | iv × 4 (qw) | 6 | 5 | 18.71 ± 2.78** | 0.13 ± 0.02** | 99.24 |
| DTX-AI lyophilized powder for injection L | 20 | iv × 4 (qw) | 6 | 6 | 25.52 ± 0.99 | 6.62 ± 2.10** | 62.38 |
| DTX-AI lyophilized powder for injection M | 40 | iv × 4 (qw) | 6 | 6 | 24.07 ± 1.19* | 0.13 ± 0.03** | 99.28 |
| DTX-AI lyophilized powder for injection H | 60 | iv × 4 (qw) | 6 | 6 | 24.24 ± 1.43 | 0.09 ± 0.02** | 99.50 |
| DTX-AI lyophilized powder for injection HH | 80 | iv × 4 (qw) | 6 | 6 | 20.99 ± 2.86** | 0.13 ± 0.05** | 99.27 |

*P < 0.05, **P < 0.01, as compared with Control

Figure 8:
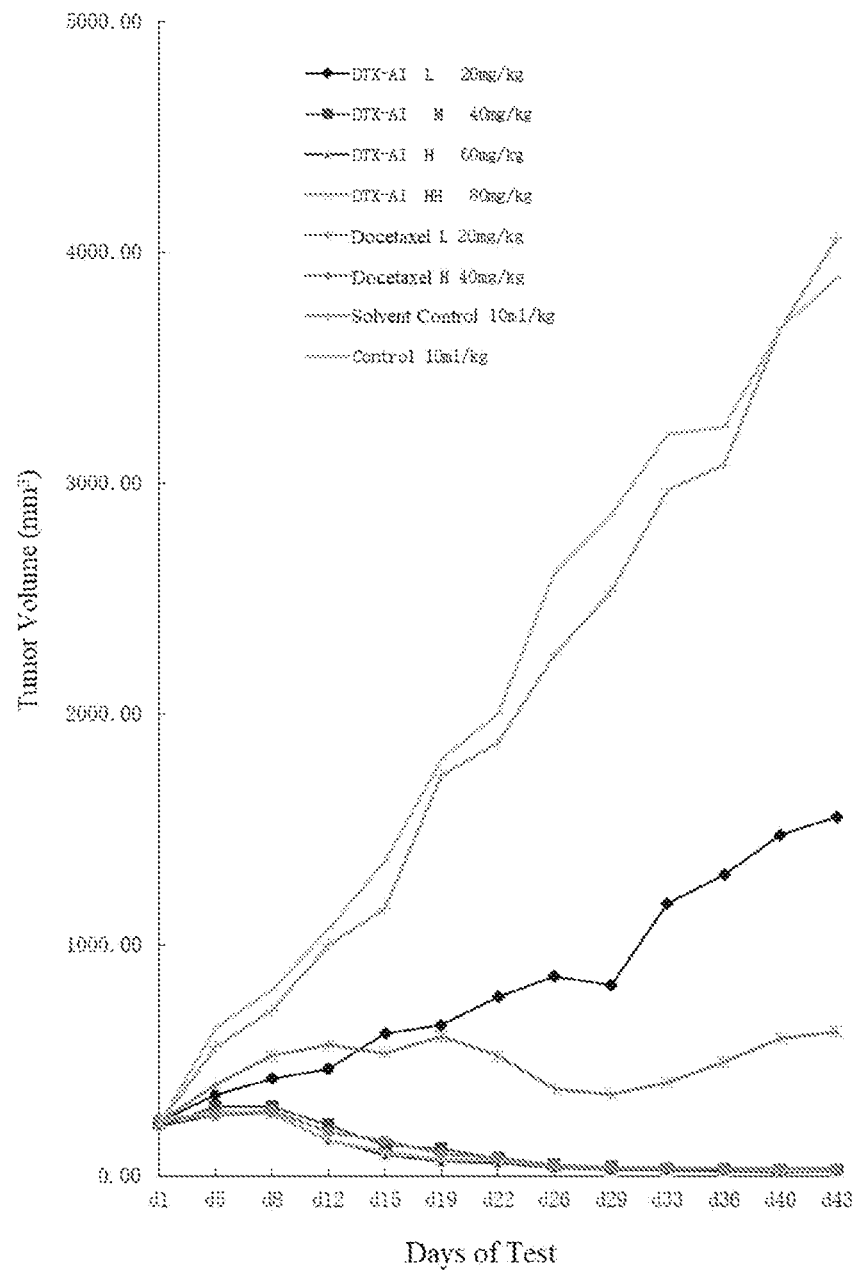
FIG. 8 shows volume changes of the xenograft tumors during the treatment in the nude mice bearing human lung cancer A549 xenograft.

The experimental results, as in Table 1 and FIG. 8, showed that the four doses (i.e. 80 mg/kg, 60 mg/kg, 40 mg/kg, and 20 mg/kg) of DTX-AI lyophilized powder, which were intravenously injected via tail vein once a week for a total of 4 times, respectively achieved the following tumor inhibition rates against A549 human lung cancer cells on the 21st day from the last administration: 99.27%, 99.50%, 99.28%, and 62.38%. Two doses (i.e. 40 mg/kg and 20 mg/kg) of docetaxel injection, which were intravenously injected via tail vein once a week for a total of 4 times, respectively achieved the following tumor inhibition rates against A549 human lung cancer cells on the 21st day from the last administration: 99.24% and 84.50%.

No death occurred in the 4 dose groups of DTX AI lyophilized powder. There was no death in the docetaxel group (20 mg/kg), and 1 animal in the 40 mg/kg group died on Day 33.

Figure 9:
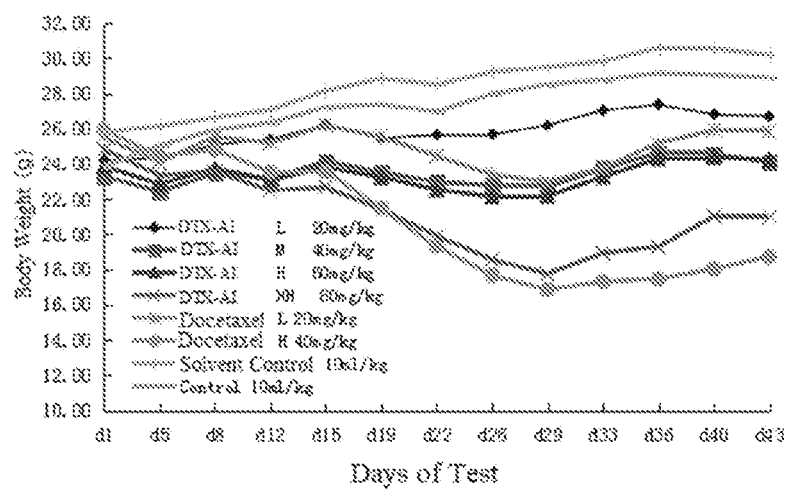
FIG. 9 shows body weight changes of the nude mice bearing human lung cancer A549 xenograft during the treatment.

As shown in Table 1 and FIG. 9, the body weights of the animals were basically not affected after administering 20 mg/kg of DTX-AI lyophilized powder, the body weights were slightly reduced after administering 40 mg/kg or 60 mg/kg of DTX-AI lyophilized powder, and the body Is weights of the animals were reduced after administering 80 mg/kg of DTX-AI lyophilized powder. The body weights of the animals were reduced after administering 20 mg/kg of docetaxel, and the body weights were gradually recovered after drug withdrawal; the body weights of the animals were severely reduced as the times of administration (40 mg/kg of docetaxel) increased, and the body weights remained low after drug withdrawal. The degree of weight loss after administering 40 mg/kg of docetaxel was significantly higher than that after administering DTX-AI lyophilized powder. Although the body weights of the animals were also reduced after administering 80 mg/kg of DTX-AI lyophilized powder, the degree of weight loss thereof was also lower than that of the docetaxel administration group (40 mg/kg).

As shown in FIG. 8, in the 4 dose groups of DTX-AI lyophilized powder, the tumor growth began to slow down after the first administration, and as the times of administration increased, the tumor inhibitory effect was enhanced. In the 40 mg/kg group, 60 mg/kg group and 80 mg/kg group, as the time period of drug withdrawal extended, the tumor inhibitory effect was maintained at 98% to 99%, and after drug withdrawal, no tumor rebound occurred in those animals.

The above data showed that as compared with the docetaxel preparations used clinically at present, the ketone carbonyl-introduced hydrophobic antitumor drugs and the pH-responsive nano preparations had better anticancer activity, higher tumor inhibition rates and higher safety in the treatment process of malignant tumors, thus having potential clinical application value.

Those disclosed above are only a few specific examples of the present application, however, the present application is not limited thereto, and any changes that may be thought of by those skilled in the art should fall within the protection scope of the present application.

What is claimed is:

1. A ketone carbonyl-containing hydrophobic antitumor drug, which is obtained by reacting (i) an isocyanate group in a compound containing both an isocyanate group and a ketone carbonyl group; with (ii) a hydroxyl group in a hydroxyl-containing hydrophobic antitumor drug,
    wherein the compound containing an isocyanate group and a ketone carbonyl group is p-isocyanate acetophenone, m-isocyanate acetophenone, o-isocyanate acetophenone, p-isocyanate benzophenone, m-isocyanate benzophenone, or o-isocyanate benzophenone,
    wherein the hydroxyl-containing hydrophobic antitumor drug is at least one selected from paclitaxel, docetaxel, a paclitaxel derivative, and a docetaxel derivative,
    wherein the paclitaxel derivative includes 10-deacetyl paclitaxel having a structure represented by Formula III, or cephalomannine having a structure represented by Formula IV:

Formula III

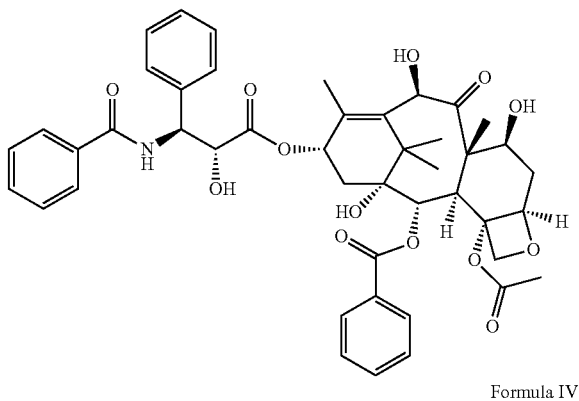

Formula IV

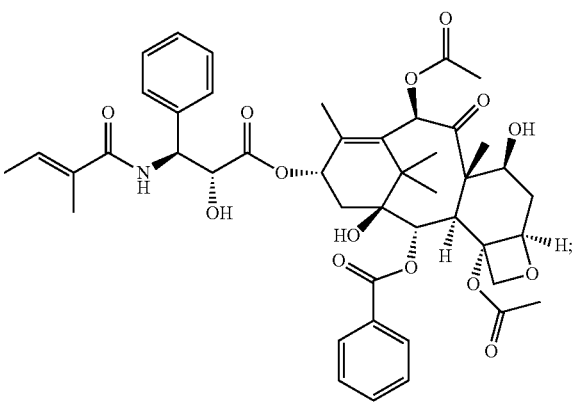

and
wherein the docetaxel derivative comprises a structure represented by Formula V:

Formula V

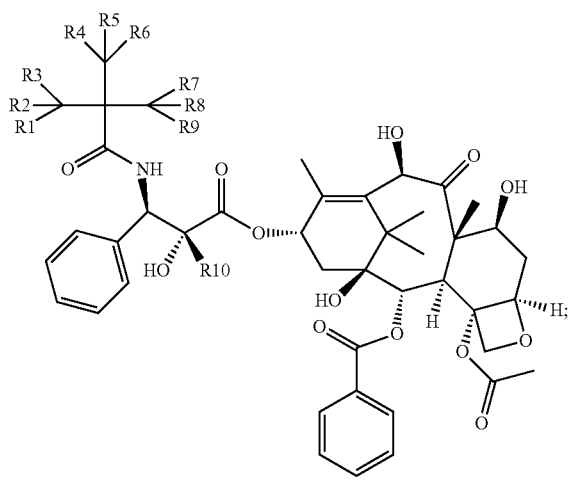

and
wherein R1, R2, R3, R4, R5, R6, R7, R8, R9 and R10 are each independently hydrogen, deuterium or fluorine, provided that at least one of R1, R2, R3, R4, R5, R6, R7, R8, R9 and R10 is deuterium or fluorine.

2. A ketone carbonyl-containing docetaxel derivative, which is obtained by reacting an isocyanate group in a compound containing the isocyanate group and a ketone carbonyl group with a hydroxyl in docetaxel or deuterated docetaxel; and the compound containing the isocyanate group and the ketone carbonyl group is p-isocyanate acetophenone, m-isocyanate acetophenone, o-isocyanate acetophenone, p-isocyanate benzophenone, m-isocyanate benzophenone, or o-isocyanate benzophenone, wherein the deuterated docetaxel has a structure represented by Formula V:

Formula V

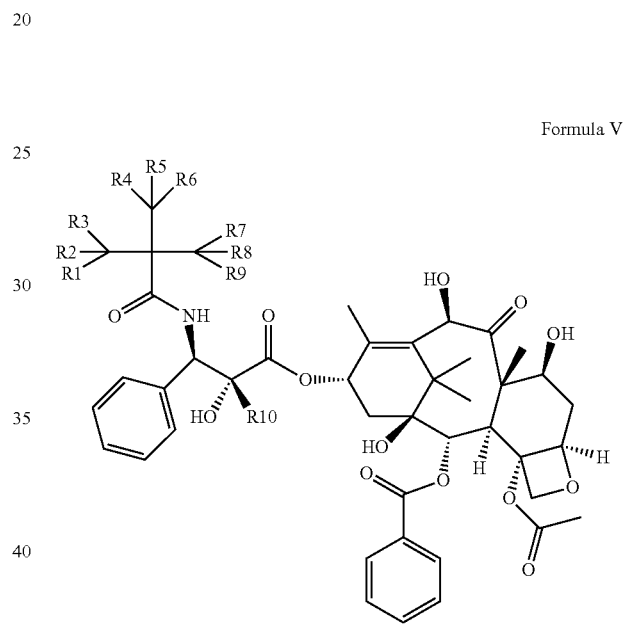

wherein R1, R2, R3, R4, R5, R6, R7, R8, R9, and R10 are each independently hydrogen, deuterium or fluorine, provided that at least one of them is deuterium or fluorine.

3. The drug according to claim 1, wherein one or more of R1, R2, R3, R4, R5, R6, R7, R8, and R9 is deuterium; and R10 is deuterium.

4. The ketone carbonyl-containing docetaxel derivative according to claim 2, wherein one or more of R1, R2, R3, R4, R5, R6, R7, R8, and R9 is deuterium; and R10 is deuterium.

* * * * *